United States Patent
Boyle et al.

[11] Patent Number: 6,001,554
[45] Date of Patent: Dec. 14, 1999

[54] ENCAPSULATION OF OLEOPHILIC SUBSTANCES AND COMPOSITIONS PRODUCED THEREBY

[75] Inventors: Stasia Boyle, Wayne; Kuei-Tu Chang, Mountain Lakes, both of N.J.

[73] Assignee: Roche Vitamins Inc., Parsipanny, N.J.

[21] Appl. No.: 09/008,251

[22] Filed: Jan. 16, 1998

Related U.S. Application Data

[63] Continuation of application No. 08/439,787, May 24, 1995, which is a continuation-in-part of application No. 08/269,720, Jul. 1, 1994.

[51] Int. Cl.⁶ ............................... C12Q 1/00; C07H 1/00
[52] U.S. Cl. .................. 435/4; 536/1.11; 536/123.1; 536/123.13; 536/56; 568/824; 552/653; 552/299; 549/408
[58] Field of Search ...................... 435/4; 536/1.11, 536/123.1, 123.13, 56; 568/824; 552/653, 299; 549/408

[56] References Cited

U.S. PATENT DOCUMENTS

| | | | |
|---|---|---|---|
| 4,084,012 | 4/1978 | Krumel et al. | 435/4 |
| 4,182,778 | 1/1980 | Hall et al. | 435/4 |
| 4,389,419 | 6/1983 | Lim et al. | |
| 4,415,703 | 11/1983 | Toba et al. | |
| 4,716,041 | 12/1987 | Kjornaes et al. | 435/4 |
| 4,734,285 | 3/1988 | Alderman et al. | 435/4 |
| 4,834,985 | 5/1989 | Elger et al. | 435/4 |
| 4,880,830 | 11/1989 | Rhodes | 435/4 |
| 4,952,402 | 8/1990 | Sparks et al. | 435/4 |
| 4,973,469 | 11/1990 | Mulligan et al. | 435/4 |
| 4,997,454 | 3/1991 | Violante et al. | 435/4 |
| 5,008,254 | 4/1991 | Weibel | 435/4 |
| 5,024,842 | 6/1991 | Edgren et al. | 435/4 |
| 5,051,261 | 9/1991 | McGinity et al. | 435/4 |
| 5,223,268 | 6/1993 | Stetsko et al. | 435/4 |
| 5,456,985 | 10/1995 | Zgoulii et al. | 435/4 |

FOREIGN PATENT DOCUMENTS

| | | |
|---|---|---|
| 462 003 | 12/1991 | European Pat. Off. |
| 595 030 | 5/1994 | European Pat. Off. |
| 88/08300 | 11/1988 | WIPO |
| 89/07935 | 9/1989 | WIPO |

OTHER PUBLICATIONS

CA111(14): 120795v CA. (1989).
CA107(18): 161576k CA. (1987).
CA104(14): 116022d CA. (1986).
CA104(10): 75045t CA. (1986).
CA98(4): 22195t CA. (1983).
CA92(10): 82322t CA. (1980).
CA92(18): 153174j CA. (1980).
CA97(22): 188273w CA. (1982).
CA87(2): 11531w CA. (1977).
CA88(8): 55023g CA. (1977).
CA87(2): 11530v CA. (1977).
CA88(25): 188466a CA. (1978).
CA86(26): 195172p CA. (1977).
CA85(22): 166578z CA. (1976).
CA83(4): 33066t CA. (1975).

*Primary Examiner*—Louise N. Leary
*Attorney, Agent, or Firm*—Mark E. Waddell; Stephen M. Haracz; Bryan Cave LLP

[57] ABSTRACT

Multiple micro-encapsulations of a high concentration oleophilic substance using heat to set the primary particle renders the composition suitable for the production of free-flowing powders or beadlets. Microencapsulation involves forming an emulsion out of the oleophilic substance and a polymer, and then use heat setting and/or cross-linking the polymer encapsulates the oleophilic composition. This process is then repeated with a second polymer or third polymer, and with or without cross-linked via the same or different mechanism to further protect the oleophilic substance.

29 Claims, 5 Drawing Sheets

ENCAPSULATION OF OLEOPHILIC SUBSTANCES AND COMPOSITIONS PRODUCED THEREBY

CROSS-REFERENCE APPLICATION

This is a continuation of U.S. Ser. No. 08/439,787, filed May 24, 1995, which is a continuation-in-part of U.S. Ser. No. 08/269,720, filed Jul. 1, 1994.

FIELD OF THE INVENTION

The invention relates to encapsulation of oleophilic substances (as used herein the term "oleophilic" is to embrace fat- and oil-soluble substances as well as fats and oils), and to compositions produced by this process. In particular, the invention relates to the preparation of high potency, dry and free-flowing vitamin powders/beadlets using multiple microspheric and/or microencapsulation techniques.

BACKGROUND OF THE INVENTION

Oleophilic substances, and in particular fat-soluble vitamins such as A, D, E and K, have had limited incorporation into dry materials because of their oil-like nature. Accordingly, oleophilic substances have tended to be macroencapsulated and delivered as units of coated oil. Unfortunately, however, such delivery drastically restricts the applications for which these oleophilic substances are suitable. For example, current commercial techniques can only produce concentrations of vitamin E which range up to 50% by weight.

The present invention overcomes the limitations inherent in the prior art encapsulation techniques and allows for production of high potency vitamins in a free flowing powder form. Such a form allows for delivery into multiple vitamin tablets or foods, such as cereal, and provides the advantages of reducing tablet size or the bulk required for subsequent delivery. Of particular interest is high potency Vitamin E in which Vitamin E forms greater than about 50% by weight of a dry powder or beadlet.

The prior art, as represented by Lim, et al., U.S. Pat. No. 4,389,419, issued Jun. 21, 1983, the contents of which are herein incorporated by reference, describes the formation of an emulsion consisting of a continuous phase aqueous solution of an alkali metal alginate, and optionally, a water-soluble alcohol-insoluble filler such as a polysaccharide, and a dispersed phase of an oleophilic substance. The emulsion thus produced is then formed into droplets which are emersed into an alcoholic solution of multi-valent cations, to produce a water-insoluble shape-retaining alginate matrix filled with precipitated polysaccharide and enclosing plural oil droplets.

The Lim, et al. approach differs markedly from that of the subject invention in which an oleophilic substance is incorporated into a primary polymer containing solution, and then solidified under mixing conditions to encapsulate the fat-soluble substance and form an encapsulated fat-soluble composition. Through the use of mixing conditions in forming the primary particle, far greater concentrations of oleophilic substances relative to those achieved by Lim, et al. can be realized. As stated by Lim, et al., the amount of oil may range from between 1% up to nearly 30%. However, at the higher end of this range, the stability of the Lim, et al. oil-in-water emulsion is decreased and the quality of the Lim, et al. microcapsule is reduced. Additionally, the Lim, et al. droplets need to be removed from the alcoholic solution and washed, or otherwise treated, to remove any residual alcohol, thus requiring extra production steps.

Another markedly different approach employed for encapsulating vitamin or mineral nutrients, such as thiamine, is described by Hall, et al., U.S. Pat. No. 4,182,778, issued Jan. 8, 1980, the contents of which are herein incorporated by reference. Hall, et al. describes encapsulation by fluidizing the nutrient in a gaseous stream and contacting the nutrient with finely atomized droplets of a coating solution. Nowhere, however, is the application of the Hall, et al. suggested for use with oleophilic substances.

As described below, the concentration of the oleophilic substance in the subject invention typically ranges from about 30% to about 90% based on the dry weight percentage of the final encapsulated oleophilic composition. These percentages are far superior to those described by Lim, et al., and form a major breakthrough over the current state of the art which only allows percentages of vitamin E to reach about 50%. Thus, the subject invention fulfills a long-felt need in the art for a high potency encapsulated oleophilic composition.

SUMMARY OF THE INVENTION

The invention provides a method for producing a composition which encapsulates an oleophilic substance. This method comprises incorporating an oleophilic substance into a primary polymer-containing solution, and solidifying the primary polymer under mixing conditions to encapsulate the oleophilic substance within the polymer and form the composition.

Typically, the primary polymer is a cellulose, such as methylcellulose and hydroxypropyl methylcellulose, and the oleophilic substance is a fat-soluble vitamin, such as vitamin A, D, E, and K. Preferably, the concentration of the oleophilic substance ranges from about 30% to about 90% based on a dry weight percentage of the final encapsulated composition.

Also provided is a preferred method for producing a composition encapsulating an oleophilic substance. This method involves incorporating an oleophilic substance into a primary polymer-containing solution, solidifying the primary polymer under mixing conditions to encapsulate the oleophilic substance within the polymer and form a primary particle, and adding a secondary polymer under mixing conditions to further encapsulate at least one primary particle within the secondary polymer and form the composition (secondary particle). Of course, multiple primary particles may be encapsulated to form a single secondary particle, and the mixing conditions may vary between the first and second encapsulation.

As with the first method, the primary polymer is usually a cellulose, such as methylcellulose and hydroxypropyl methylcellulose. The secondary polymer is generally a cellulose, cellulose derivative, maltodextrin, such as a maltodextrin having a dextrose equivalent value of about 18, alginate, calcium lactate, acacia, gelatin, such as fish gelatin, or modified starch, such as hydroxypropyl starch or pregelatinized corn starch.

Preferred celluloses include methylcellulose and hydroxypropyl methylcellulose, and preferred cellulose derivatives include hydropropylmethyl cellulose phthalate.

In a preferred embodiment, the secondary polymer is used to encapsulate the primary particle. Such encapsulation may be achieved by changing the pH, by adding a cross-linking agent, by heating, by spray drying, or by other suitable means. Example of cross-linking agents include sugar, acacia, cations, or gelatin.

Further provided by the subject invention are compositions produced by the above methods.

One composition encapsulating an oleophilic substance comprises an oleophilic substance, a first polymer which encapsulates the oleophilic substance to form a primary particle, and a second polymer which encapsulates at least one primary particle. The choices of primary and secondary polymers are as described above.

DETAILED DESCRIPTION OF THE INVENTION

Figure 1:
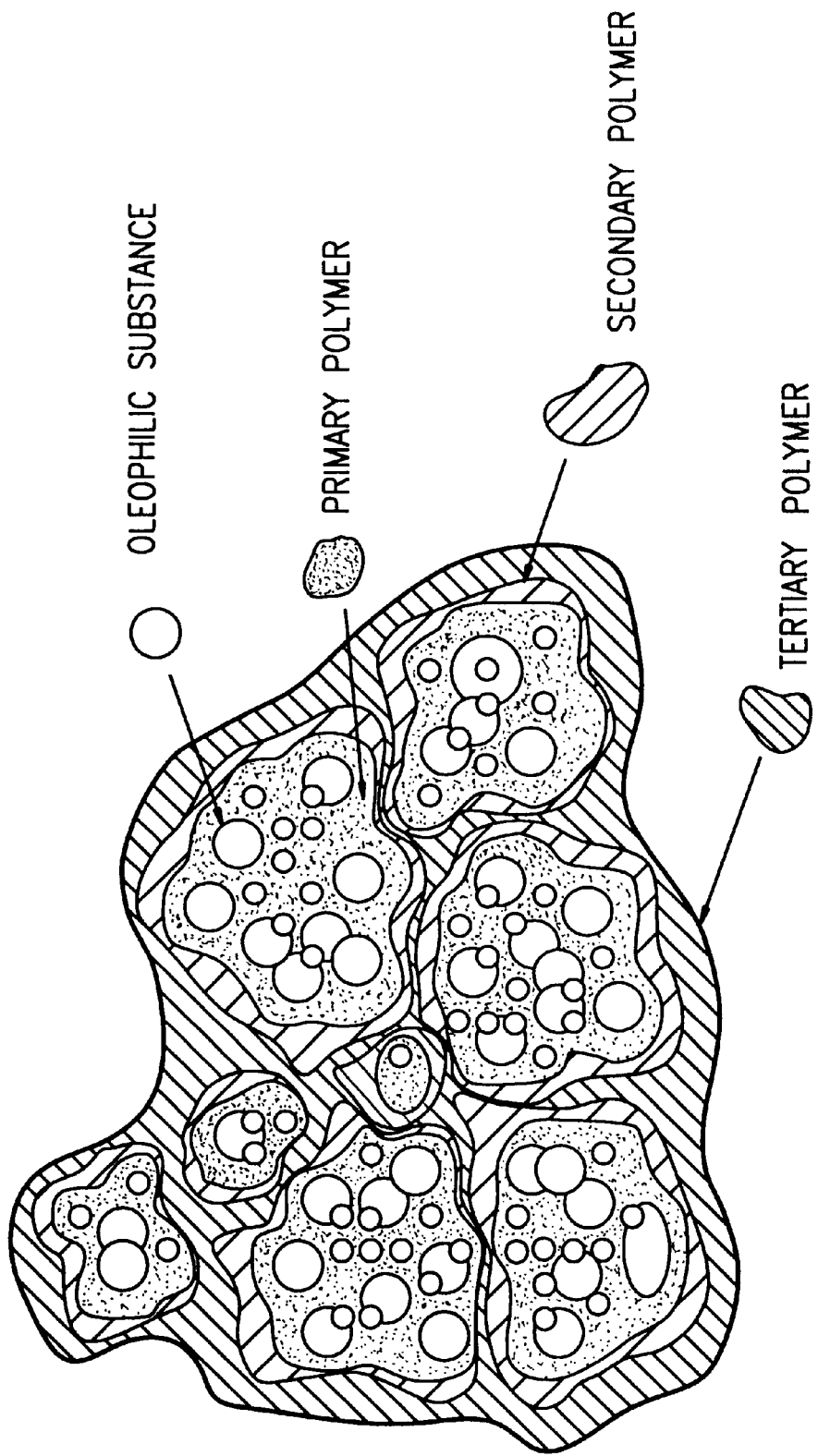
FIG. 1—An illustration of a powder/beadlet showing the multi-microencapsulation structure formed in one embodiment of the present invention.
Figure 2:
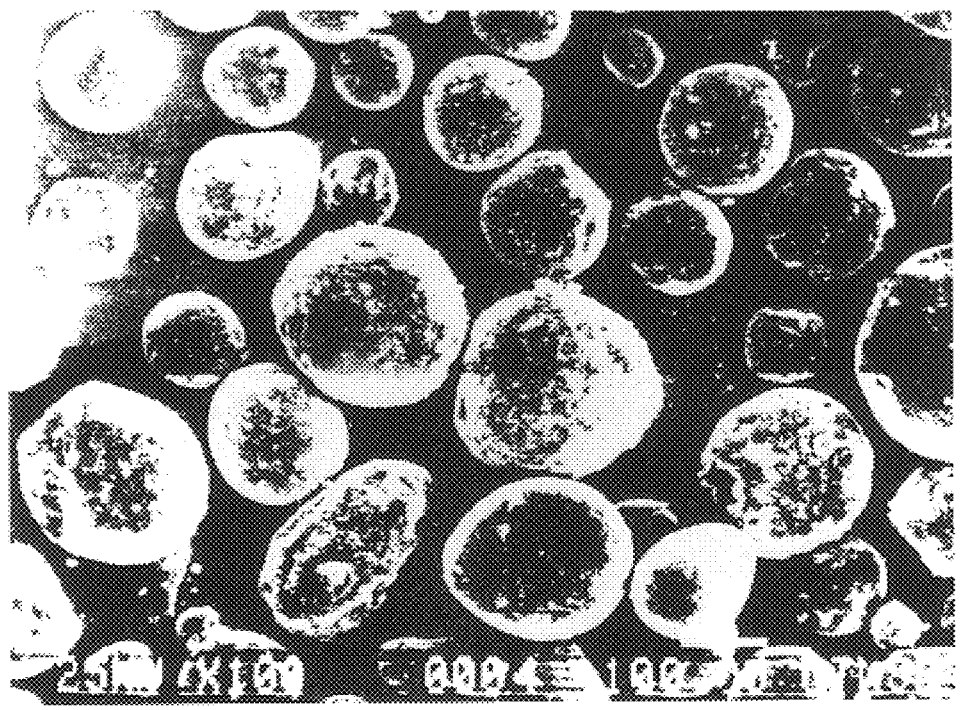
FIG. 2—A scanning electron micrograph (SEM) of a vitamin E powder (X100).
Figure 3:
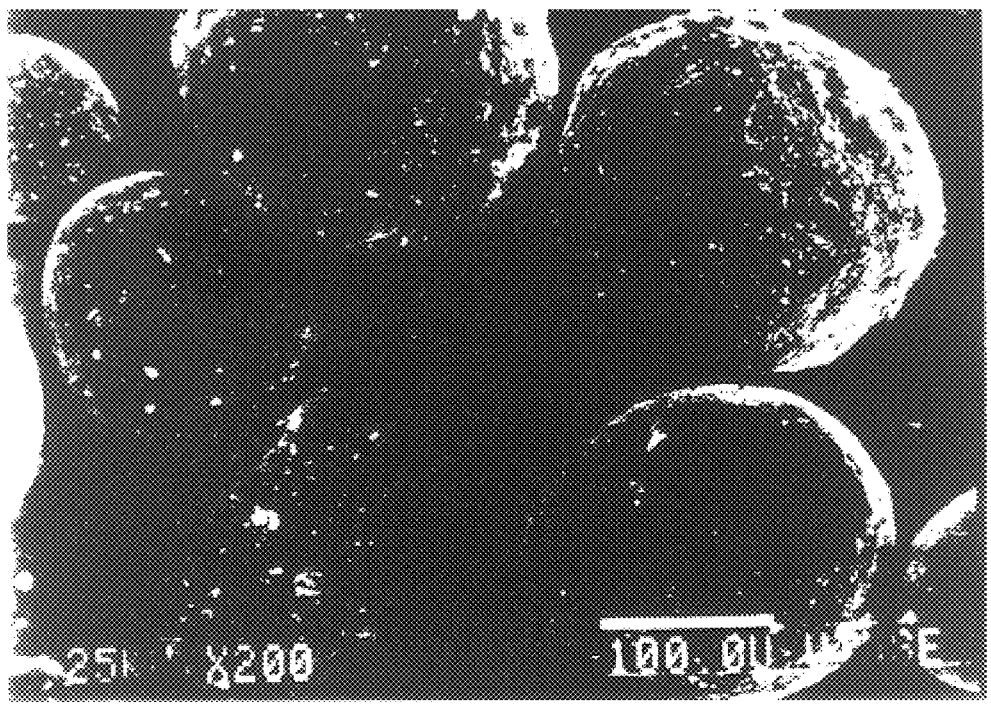
FIG. 3—SEM of a vitamin E powder (X200).
Figure 4:
FIG. 4—SEM of sectioned vitamin E powder (X100).
Figure 5:
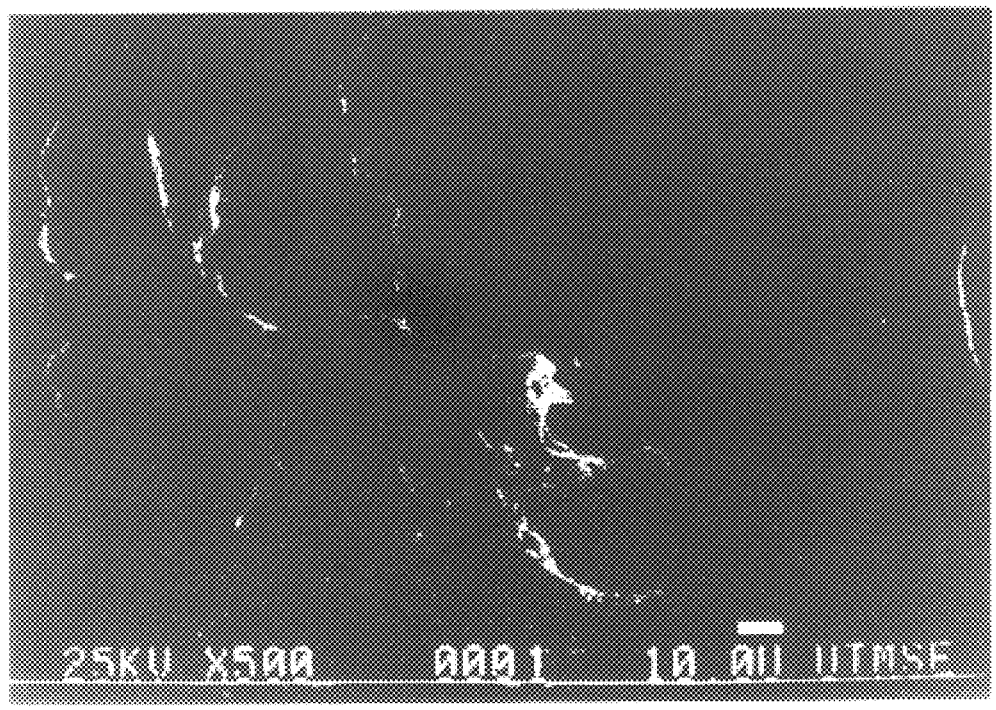
FIG. 5—SEM of sectioned vitamin E powder (X500).

The invention will now be described in terms of its preferred embodiments. These embodiments set forth to aid in the understanding of the invention, but are not to be construed as limiting. Throughout the specification, percentages are by weight percent and temperatures are °C., unless noted otherwise.

One inventive aspect of the subject invention is the production of high potency (generally from about 30 to about 90 weight percent) fat-soluble vitamins (such as A, D, E and K) in the form of dry powders and/or beadlets.

These vitamin powders and/or beadlets can be prepared by (1) emulsifying vitamin oils (such as vitamins A, D, E or K) in a polymeric solution (such as a cellulose or cellulose derivative), (2) dispersing vitamins (present as crystals) in a polymeric solution to form a suspension, or (3) dissolving and/or diluting fat-soluble vitamins in oil, then emulsifying the vitamin-oil solution in a polymeric solution to form an emulsion. Typically, the polymeric solution will be an aqueous solution.

Then, after the emulsifying, dispersing, dissolving and/or diluting, the emulsion or suspension is heated to a polymeric setting temperature (typically greater than 50° C.) under mixing conditions to produce primary particles (e.g., microcapsules and/or microspheres). Alternatively, the polymer can be cross-linked. In each of these three above scenarios, the oleophilic substance is present as a liquid during at least a portion of the processing time, and typically throughout processing.

For ease in describing the subject invention, emulsifying, dispersing, dissolving and diluting will collectively be referred to as "incorporating."

The term "mixing conditions" refers to a state of imparted movement, such as that associated with stirring, shaking, agitating, jumbling, etc., which is vigorous enough to cause the emulsion or suspension to solidify as particles. Mixing conditions are readily determined by a skilled artisan who has read the present specification using known techniques, for example, by using an anchor stirrer, homogenizers, colloidal mills, microfluidizers, sonicators, or impellers (mechanical stirring). Particle size can be varied by changing the amount of imparted movement. For example, slow stirring will generally produce a larger particle size than will fast stirring. The examples which follow provide ample guidance for one skilled in the art to determine appropriate mixing conditions without undue experimentation.

Microcapsules are formed by a single encapsulation, whereas microspheres are conglomerates of multi-oil droplets embedded in a spherical or sphere-like matrix. The term "primary particle" as used herein refers to micro- and/or macro-particles produced by either heat inducing (setting), coacervating or cross-linking a polymer-containing emulsification. For convenience, cross-linking, coacervating and thermal setting will collectively be referred to as "solidifying."

Theoretically, preparation of oleophilic substances in a primary polymer-containing solution to form an emulsion or suspension can be performed at any temperature. However, the practical temperature range for this step depends on the nature of polymer chosen. For example, in preparing an HPMC emulsion, the preferred temperature should be between room temperature and no higher than 60° C. The skilled artisan is readily able to determine an acceptable temperature range based on the components chosen.

The solidification step for making the primary particles is physically determined by the mechanism and process temperature. For instance, if solidification is caused by cross-linking, such as with an alginate emulsion cross-linking with calcium ions, temperature may not be critical. That is, processing can be effected at any temperature. However, when HPMC is chosen as the main polymer for the primary particles, and heating is the main mechanism utilized to make primary particles, temperature becomes important and must be maintained at about 60° C. throughout the whole process. Again, these parameters are determinable to the skilled artisan, having read the present disclosure.

Primary particles may then be further encapsulated with a secondary and/or tertiary (depending on whether the primary particles are microcapsules or microspheres) polymeric layer by the addition of a second polymer to the suspension followed by solidifying the second polymer (such as cross-linking by adding a cation, or by changing the pH) to form a secondary particle. The term "secondary particle" as used herein refers to a primary particle which has been further encapsulated or coated. The term "encapsulated" also includes the term "coated". Of course, multiple primary particles (at least 2) may be encapsulated or coated to form a single secondary particle.

Although the current method of production first solidifies the primary polymers by heating to form the primary particles and then simply coats or chemically cross-links the secondary polymers to form the secondary particles, alternate methods of solidifying may be utilized. Additionally, further encapsulations of the secondary particles, such as coating or polymerization around the secondary particles, may be effected.

Secondary and tertiary polymers are typically celluloses (e.g., methylcellulose or hydroxypropyl methylcellulose), cellulose derivatives (e.g., hydroxypropyl methylcellulose phthalate), alginates (e.g., sodium alginate or propylene glycol alginate), modified starches (e.g., pregelatinized corn starch or hydroxypropyl starch), calcium lactate, gelatins (e.g., fish gelatin), maltodextrins (e.g., dextrin having about 18 dextrose equivalent value, D.E.=18), or acacias. The final mixture may be sprayed dried or processed by any suitable drying techniques to powder or beadlet form which has high potency, is dry and free-flowing, and is suitable for tableting or encapsulation within soft or hard gelatin capsules. Such powders may also be used in food, animal feed, or other pharmaceutical applications, such as premix, suspension and emulsion.

The addition of secondary and/or tertiary polymer onto the primary particles is based on the same principle as described above. The proper temperatures, pH ranges, and ionic strengths for adding the second and/or third polymer varies depending on the types of materials and mechanisms used.

EXPERIMENTAL DETAIL

Example 1

High Potency Vitamin E Acetate Using Methocel E 15LV as the Primary Polymer, Sodium Alginate As the Second Polymer, and HPMC 6 cps as the Tertiary Polymer

| INGREDIENTS | FORMULA I A | FORMULA I B |
|---|---|---|
| Vitamin E acetate | 75 + 2% overage[1] | 75 + 2% overage[1] |
| Methocel E 15LV[2] | 13.0 | 20.0 |
| Kelton LV/CaCloride[3] Ratio 1:0.5 | 2.0 | 2.0 |
| HPMC, 6 cps[4] | 10.0 | 3.0 |

[1]Overage is standard in the industry to ensure that the final product contains at least the given percentage. Therefore, a 2% overage was added.
[2]Methocel E15LV refers to a special grade of hydroxypropyl methylcellulose manufactured by Dow Chemical Co.
[3]Keltone LV refers to the trade name for sodium alginate from the Kelco, Division of Merck & Co. Inc.
[4]HPMC, 6 cps refers to hydroxypropyl methylcellulose 2910; such as that manufactured by SHI-ETSU Co. ("PHARMACOAT 606"). "Cps" is the viscosity unit "centiopoise," is commonly referred to in the industry, and is referenced throughout the specification.

Procedure

1. Sodium alginate solution (5% w/w) was prepared in a 2 liter (l) beaker as follows:

| Preparation of 5% sodium alginate | | | | |
|---|---|---|---|---|
| Time (min.) | Temperature (° C.) | Stirrer speed (rpm) | Amount | Comments |
| 0 | 20 | | 1.27 l | Add water to beaker and stir |
| 5 | 20 | 1200 | 66.7 g | Add sodium alginate |
| | 25 | 2000 | | Heat suspension to 70° C., and maintain temperature and agitation until the solution is used |

2. Calcium chloride solution (5% by weight) was prepared in a 1 l beaker as follows:

| Preparation of 5% calcium chloride | | | | |
|---|---|---|---|---|
| Time (min.) | Temperature (° C.) | Stirrer | Amount | Comments |
| 0 | — | — | 0.633 l | Add water to beaker |
| 1 | | on | 33.3 g | Add calcium chloride |
| 2 | 22 | on | | Stir and maintain temperature at 70° C. until used |

3. HPMC, 6 cps solution (12% by weight) was prepared in a 5 l beaker as follows:

| 12% HPMC, 6 cps | | | | |
|---|---|---|---|---|
| Time (min.) | Temperature (° C.) | Stirrer speed (rpm) | Amount | Comments |
| 0 | 21 | | 2.45 l | Add water to beaker and heat to 90° C. |
| 32 | 90 | 1000 | 0.5 kg | Slowly add HPMC 6 cps powder with agitation |
| 52 | 86 | 200 | | Addition completed Remove heating source |
| 82 | 91 | 1000 | 1.22 l | Rapidly add cold water (rapid cooling) Cool to room temperature while maintaining gentle agitation until use |

4. Methocel E15LV solution (10%) was prepared using the same procedure as described in step 3. Essentially, Methocel E15LV was dispersed in 90° C. water, stirred and then uniformly dissolved in the water while the temperature was cooled.

5. Vitamin E acetate (an oil) was added to the Methocel solution according to the above formula, and homogenized using a colloidal mill until an emulsion having the smallest possible oil droplet size was reached. Although average droplet size tends to vary, droplets less than about 3 $\mu$m in diameter are satisfactory for most uses. Typically, average droplets range between about 0.5 and 1 $\mu$m in diameter, even though smaller diameters are generally preferred. (During emulsification, a cooling system was applied to maintain the temperature at approximately 25° C.).

6. The emulsion was then heated to about 80–90° C. while mixing slowly (at about 200 r.p.m.) with an anchor stirrer.

7. Warm (70° C.) 5% alginate solution was then added and the mixture was mixed slowly (at about 200 revolutions per minute (r.p.m.) with an anchor stirrer) while maintaining temperature above 70° C.

8. The mixture was maintained at about 70° C. for approximately 15 minutes, and then cross-linked by adding 5% calcium chloride solution.

9. HPMC 6 cps 12% solution at room temperature (RT) was added in small aliquots while maintaining the temperature above 70° C.

10. Water was then added to adjust viscosity to less than about 2,000 cps (in this particular instance 1,000 cps) for spray drying.

11. The solution was then spray dried under conventional conditions.

A specific vitamin E emulsion was prepared in a FRYMA processing unit (homogenizer, different types of mixers, and cooling and heating system) manufactured by Fryma, Inc., as follows:

Preparation of the vitamin E emulsion and suspension

| Time (min.) | Temp. (° C.) | Anchor stirrer | Colloidal mill | Dissolver | Amount | Comments |
|---|---|---|---|---|---|---|
| 0 | 26 | on | — | — | 6.5 kg | Add 10% Methocel solution to vessel |
| 10 | 26 | — | — | — | 3.83 kg | Add vitamin E acetate to above solution |
| 18 | 27 | on | on | on | | Start emulsification |
| 23 | | on | on | on | | Sample 1: particle size of oil droplets 790 nm |
| 28 | | on | on | on | | Sample 2: particle size of oil droplets 713 nm |
| 33 | | on | on | on | | Sample 3: particle size of oil droplets 768 nm |
| 33 | | on | — | — | | Emulsification ended; begin heating to 85° C. and maintain a proper agitation throughout the whole process |
| 110 | 35 | on | — | — | | Add sodium alginate solution (75° C.) |
| 115 | 83 | on | — | — | | Mix 15 minutes |
| 130 | 82 | on | — | — | | Add calcium chloride solution (75° C.) |
| 132 | 85 | on | — | — | | Add HPMC 6 cps solution (75° C.) |
| 145 | 85 | on | — | — | | Begin cooling |
| 165 | 82 | on | — | — | | Mix at room temperature |
| 195 | 22 | on | — | — | | Heat up to 75° C. |
| 245 | 19 | on | — | — | | Measure viscosity: 4300 cps |
| 255 | 73 | on | — | — | 21 | Add water to adjust viscosity to 1000 cs |

Spray dry the above vitamin E suspension using a NIRO spray dryer; operation with air. This spray dryer is manufactured by Niro, Inc.

Example 2A

High Potency Vitamin E Acetate Using Methocel E15LV as the Primary Polymer and HPMCP HP-55S as the Secondary Polymer

| INGREDIENTS | 85% E | 80% E | 75% E | 70% E | 65% E | 50% E |
|---|---|---|---|---|---|---|
| Vitamin E acetate | 85 | 80 | 75 | 70 | 65 | 50 |
| Methocel E15LV | 10.0 | 13.4 | 16.7 | 20 | 23.4 | 33.4 |
| HPMCP grade HP-55S* | 5.0 | 6.6 | 8.3 | 10 | 11.6 | 16.4 |

Note: A 2% overage for Vitamin E acetate was used for each formula.
* To dissolve HPMCP, 4.5 ml of 0.5N NaOH per gram of HPMCP was utilized. Once HPMCP completely dissolved in the alkaline solution, water was added to adjust the solution to 15% solid content.

Procedure

1. HPMCP HP-55S solution (15% by weight) was prepared in a 100 l vessel as follows:

Preparation of 15% HPMCP HP 55s Solution

| Time (min.) | Temp. (° C.) | Stirrer | Amount | Comments |
|---|---|---|---|---|
| 0 | 16 | on | 14.94 l | Add water into the vessel |
| 5 | 15 | on | 300 g | Add sodium hydroxide slowly |
| 10 | 16 | on | | Addition ended |
| 15 | | on | 3.32 kg | Add HPMCP HP-55S powder to above solution with agitation |
| 35 | 14 | on | | Addition ended, start heating |
| 215 | 65 | on | 3.57 l | Add 70° C. hot water Stir the solution until use |

2. Methocel E15LV solution (10%) was prepared as in Example 1.

3. Vitamin E acetate was added to the Methocel solution according to the above formulas and homogenized to produce an emulsion as in Example 1.

4. The resulting emulsion was heated to 80–90° C. with slow (200 r.p.m.) mixing with an anchor stirrer.

5. An amount of warm (70° C.) 15% HPMCP solution was added. The amount added corresponded to the amount recited in percentage table shown above.

6. The temperature of above mixture was kept at about 80° C. and cross-linked by adding HCl (0.1 N), with mixing, to shift the pH to approximately 5 (about 4.9–5.2).

7. The cross-linked solution was allowed to equilibrate for approximately 45 minutes.

8. The resulting cross-linked solution was then spray dried at the conditions shown below to form a powder.

Spray drying of the vitamin E suspension
The suspension was pumped from the FRYMA processing unit to the spray tower by a gear pump and then atomized by a rotary atomizer from Niro, Inc.

| Time (min.) | Set Inlet Temp. (° C.) | Inlet Temp. (° C.) | Set outlet Temp. (° C.) | Outlet Temp. (° C.) | Set Pressure Tower in mbar | Pressure Tower in mbar | In at air flow in $m^3/n$ | Comments |
|---|---|---|---|---|---|---|---|---|
| 0 | 180 | | 100 | | −5 | | | Start up lower |
| 50 | 180 | 181 | 100 | 101 | −5 | −3 | 1500 | Start spray drying |
| 60 | 180 | 181 | 100 | 100 | −5 | −3 | 1500 | |
| 62 | | | | | | | | Spray drying ended |

The "Set Pressure Tower" is the setting for the equilibrium condition in the dryer. In contrast, the "Pressure Tower" is the actual pressure reached in the dryer during spray drying.

Example 2B

High Potency Vitamin E Acetate Using Methocel E15LV as the Primary Polymer and Fish Gelatin, Maltodextrin, Pregelatinized Corn Starch, Calcium Lactate, or Hydroxypropyl Starch as the Secondary Polymer Following the procedure in Example 2A (with HPMCP being replaced by another secondary polymer), several different secondary polymers were evaluated as follows:

| INGREDIENTS | Fish Gelatin 75% E | Maltrin 75% E | Preglatinized Corn Starch 75% E | Calcium Lactate 75% E | Hydroxypropyl Starch 75% E |
|---|---|---|---|---|---|
| Vitamin E Acetate | 75 | 75 | 75 | 75 | 75 |
| Methocel E15LV | 16.7 | 16.7 | 16.7 | 16.7 | 16.7 |
| Fish Gelatin | 8.3 | — | — | — | — |
| Maltrin M180[1] | — | 8.3 | — | — | — |
| Pregelatinized Corn Starch | — | — | 8.3 | — | — |
| Calcium Lactate | — | — | — | 8.3 | — |
| Hydroxypropyl Starch | — | — | — | — | 8.3 |

[1]Brand of maltodextrin (D.E. = 18).

Analysis of the five secondary polymers provided the following results using standard test procedures:

| | | Fish Gelatin | Maltrin M180 | PreGel Starch | CaLactate | HP Starch |
|---|---|---|---|---|---|---|
| Flow (Agway) | sec./100 g | 27 | 23 | 28 | 17 | 39 |
| Density | g/ml | 0.34 | 0.39 | 0.33 | 0.50 | 0.34 |

-continued

| | | Fish Gelatin | Maltrin M180 | PreGel Starch | CaLactate | HP Starch |
|---|---|---|---|---|---|---|
| Tapped Density | g/ml | 0.39 | 0.44 | 0.38 | 0.56 | 0.39 |
| Moisture | % | 1.3 | 1.0 | 2.8 | 0.8 | 1.0 |
| Color | W1E313 | 37.87 | 54.26 | 51.43 | 53.65 | 50.10 |
| | Y1E313 | 13.22 | 9.18 | 9.96 | 9.12 | 9.94 |
| Static | observed | High | Medium | Low | Medium | Very High |
| Free Oil[5] | % | 2.4 | 1.6 | 2.3 | 2.9 | 2.2 |

[5]Free Oil refers to the percentage of unencapsulated vitamin E, and was determined as follows:

Procedure for Measuring Free Oil on Powder Surface

Procedure for Preparing Sample Solution

1. Transfer 0.250 g of powder (vitamin E 75%) to a suitable container.

2. Add 43.0 g of light mineral oil (Fisher).

3. Shake on a mechanical shaker at medium speed for 15 minutes.

4. Pass through a 0.45 μm filter.

5. Measure the UV absorption of the filtrate at 285 nm to determine the abs(sample). Compare against known vitamin E acetate standard (Std).

Procedure for Preparing Standard Solution

1. Weigh 150 mg vitamin E oil standard in a suitable container.

2. Add 86.0 g light mineral oil to above container.

3. Mix using a mechical shaker at medium speed for 15 minutes.

4. Remove 2.5 g of above solution and transfer to an appropriate container.

5. Add 43.0 g of light mineral oil to the container and shake for an additional 15 minutes.

6. Measure the u.v. absorbtion of above solution at 285 nm to determine abs(Std.).

Calculations:

$$\frac{X(g)/43.0}{0.150/(0.150+86.0) \times 2.5/(2.5+43.0)} = \frac{X(g)}{0.004114}$$

$$X(g) = \frac{\text{abs(Sample)}}{\text{abs(Std.)}} \times 0.004114$$

% Free Oil in powder (% unencapsulated vitamin E)=X/(0.25×0.75)×100

Procedure for Evaluating Powder Suitability for Tabletting

The powders of the subject invention are useful in producing antioxidant tablets. To demonstrate their suitability and tabletting performance in antioxidant tablets, tablets were prepared at 4,000 lb pressure using a rotary press.

TABLETTING PERFORMANCE OF VITAMIN E75% POWDERS IN ANTIOXIDANT TABLETS AT 4000 LB PRESSURE USING ROTARY PRESS

| | | | | | | |
|---|---|---|---|---|---|---|
| Ejection Force | lbs | 47 | 40 | 41 | 38 | 43 |
| Hardness Avg | scu | 15 | 17.1 | 16.9 | 12.3 | 12.9 |
| Range | | 11.7–16.9 | 15.6–18.3 | 15.8–18 | 11.1–13.6 | 11.8–13.6 |
| Disintegration | minutes | 15 | 15 | 20 | 14 | 14 |
| Friability | % | 0.03 | 0.07 | 0.09 | 0.08 | 0.09 |

The above results were obtained using the following antioxidant formula:

ANTIOXIDANT FORMULA
USING VITAMIN E75, BETATAB R AND C-90 GLOBAL

| Ingredients | claim tablet | % overage | mg/tab | % | kg/90 kg Batch |
|---|---|---|---|---|---|
| BetaTab R 7.5% (Beta Carotene 7.5% Beadlets) | 6 mg | 35 | 108 | 11.55 | 10.395 |
| Vitamin C-90 Global | 250 mg | 5 | 292 | 31.23 | 28.107 |
| Vitamin E 75% | 200 IU | 5 | 280 | 29.95 | 26.955 |
| Microcel C (Calcium Silicate) | | | 97 | 10.37 | 9.333 |
| Avicel PH 102 (Microcrystalline cellulose) | | | 56 | 5.99 | 5.373 |
| Polyplasdone XL (Crospovidone) | | | 97 | 10.37 | 9.333 |
| Cab-O-Sil | | | 5 | 0.54 | 0.486 |
| (Colloidal Silicon Dioxide) | | | | | |
| TOTAL | | | 935 | 100 | 90 |

Example 3

High Potency E Formula III Containing Acacia

| Ingredients | 75% E | 80% E |
|---|---|---|
| 1. Vitamin E Acetate | 75.0* | 80.0* |
| 2. HPMC E15LV | 15.0 | 12.0 |
| 3. Acacia | 10.0 | 8.0 |
| Total | 100.0% | 100.0% |

*Additional 2% overage was added.

Procedure

1. Gum acacia solution (20% by weight) was prepared in a 4 l beaker as follows:

Preparation of 20% gum acacia

| Time (min.) | Temp. (° C.) | Stirrer | Amount | Comments |
| --- | --- | --- | --- | --- |
| 0 | 21° C. | on | 2 l | Add water into beaker |
| 151 | 39° C. | on, slow | 0.5 kg | Add gum acacia |
| 175 | 36° C. | on, fast | | Addition completed |
| 190 | 37° C. | on, fast | | Begin heating |
| 208 | 63° C. | on, slow | | |
| 279 | 71° C. | — | | Add to emulsion |

2. 10% Methocel E 15LV solution was prepared as in Example 1.

3. Vitamin E acetate was added to Methocel solution according to the above formulas and homogenized to produce an emulsion as in Example 1.

4. The resulting emulsion was heated to 80–90° C. with slow (200 r.p.m.) agitation.

5. An appropriate amount of 20% acacia solution from step 1 was added.

6. The mixture from above was blended with gentle agitation for an additional 15 minutes while the temperature were maintained at 70–90° C.

7. Spray the vitamin E suspensions at the following conditions.

Spray drying of the vitamin E suspension
The suspension was pumped from the FRYMA processing unit to the spray tower by a gear pump and then atomized by a rotary atomizer manufactured by Niro, Inc.

| Time (min.) | Set Inlet Temp. (° C.) | Inlet Temp. (° C.) | Set outlet Temp. (° C.) | Outlet Temp. (° C.) | Set Pressure Tower in mbar | Pressure Tower in mbar | In at air flow in m³/n | Comments |
| --- | --- | --- | --- | --- | --- | --- | --- | --- |
| 0 | 180 | | 100 | | −5 | | | Start up lower* |
| 50 | 180 | 181 | 100 | 101 | −5 | −3 | 1500 | Start spray drying |
| 60 | 180 | 181 | 100 | 100 | −5 | −3 | 1500 | |
| 62 | | | | | | | | Spray drying ended |

*Shorthand for start up the spray dryer from a lower inlet temperature. It is standard procedure to start up a spray dryer at low temperature, then gradually increase the inlet temperature to reach a proper outlet temperature, and to establish an equilibrium condition.

Example 4

30% Vitamin A Products Using Hydroxypropyl Methylcellulose as the Primary Polymer, and Sodium Alginate, HPMCP HP-55, or Acacia as the Secondary Polymer

| Ingredient | Formula I | Formula II | Formula III |
| --- | --- | --- | --- |
| Vitamin A Palmitate | 30.0 + 2.5* | 30.0 + 2.5* | 30.0 + 2.5* |
| Butylated Hydroxyanisole (BHA) | 1.0 | 1.0 | 1.0 |
| Butylated Hydroxytoluene (BHT) | 3.0 | 3.0 | 3.0 |
| Methocel E15LV | 50.8 | 42.4 | 50.8 |
| HPMCP, HP-55S | — | 21.1 | — |
| Acacia | — | — | 12.7 |
| Sodium Alginate | 3.4 | — | — |
| Calcium Chloride | 1.7 | — | — |
| PHARMACOAT 606 | 7.6 | — | — |

Note: *% Overage

Procedure

Formulation I

Composition

| Material | content (%) | weight (kg) |
| --- | --- | --- |
| Vitamin A palmitate 1.7 MIU/g | 32.47 | 1.30 |
| BHA | 1 | 0.04 |
| BHT | 3 | 0.12 |
| METHOCEL E15LV premium | 50.82 | 2.03 |
| Sodium alginate | 3.39 | 0.136 |
| Calcium chloride | 1.69 | 0.068 |
| PHARMACOAT 606 | 7.62 | 0.305 |

General

All the solutions were prepared using degassed deionized water under nitrogen. Vitamin A palmitate was shielded from light.

Preparation of a 12% solution of METHOCEL E15LV

Water (8 l) was heated to 85° C. METHOCEL E15LV powder (2.03 kg) was slowly added into the water while mixing with rapid agitation until a uniform suspension was obtained and thoroughly dispersed. Additional cold water (6.89 l) was quickly added to the suspension and the temperature was cooled to 25° C.

Preparation of a 5% solution of sodium alginate

Sodium alginate powder (0.136 kg) was added into 2.58 liters of cold water with proper agitation and heated to 80–90° C. The solution was kept at 70° C. until used.

Preparation of a 5% solution of calcium chloride

Calcium chloride (0.068 kg) was dissolved in 1.29 l of water. The solution was kept at room temperature until used.

Preparation of a 12% solution of PHARMACOAT 606

Water (0.75 l) was heated to 90° C. PHARMACOAT 606 powder (0.305 kg) was slowly added into the water while mixing with proper agitation until a uniform suspension was formed. Cold water (1.50 l) was added quickly to the suspension and the temperature was cooled to 25° C. The solution was maintained at room temperature with gentle agitation until used.

Preparation of the emulsion/suspension

BHA (0.04 kg) and 0.12 kg BHT were added to 1.3 kg vitamin A palmitate and mixed until a clear solution was formed. The resulting solution was added to the METHOCEL E15LV solution and emulsified for 30 minutes with the colloidal mill. (The oil droplet size measured using a MALVERN Autosizer was 757 nm). The emulsion was then heated to 75° C. while slowly mixing (200 r.p.m.) with an anchor stir bar to form a suspension. The 70° C. sodium alginate solution was added to the suspension and stirred for 15 minutes. Calcium chloride solution was added, and the mixture was cooled. PHARMACOAT solution was added at room temperature and mixed for 10 minutes. The mixture was then heated to 65° C. while mixing slowly with an anchor stir bar. (the suspension had a viscosity of 11,400 cps/65° C.). The suspension was then diluted with 2 l hot water to adjust the viscosity to 2,500 cps/65° C.

Spray drying

Figure 6:
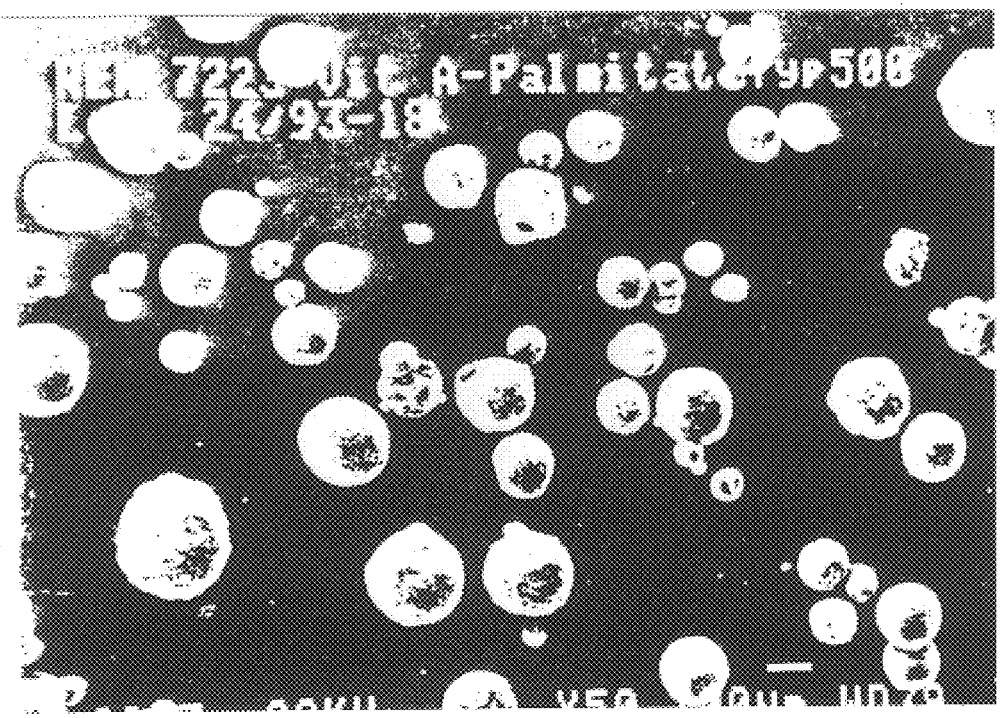
FIG. 6—SEM of vitamin A-palmitate (X50).
Figure 7:
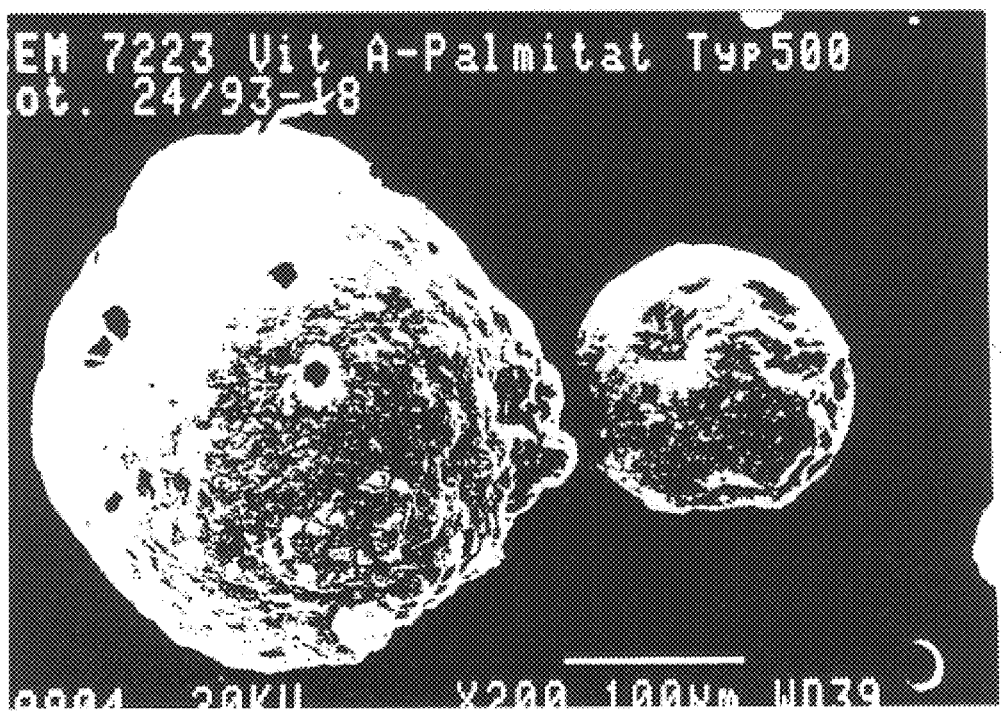
FIG. 7—SEM of vitamin A-palmitate (X200).
Figure 8:
FIG. 8—SEM of sectioned vitamin A-palmitate (X300).
Figure 9:
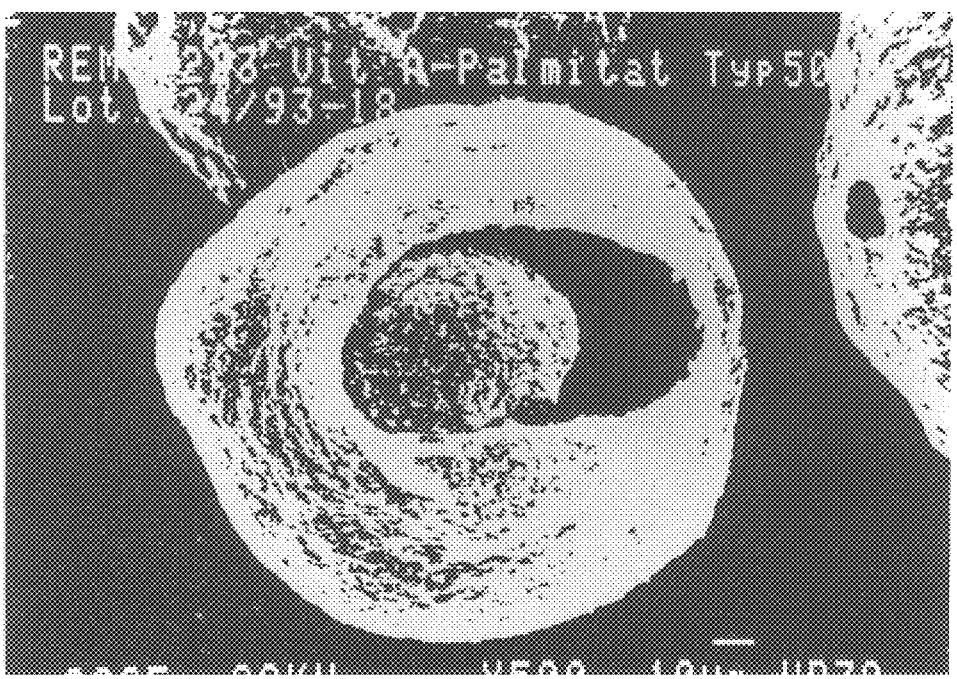
FIG. 9—SEM of sectioned vitamin A-palmitate (X500).

See below (spray dry results are shown in FIGS. 6–9).

Formulation II

Composition

| Material | content (%) | weight (kg) |
| --- | --- | --- |
| Vitamin A palmitate 1.7 MIU/g | 32.47 | 1.46 |
| BHA | 1 | 0.045 |
| BHT | 3 | 0.135 |
| METHOCEL E15LV premium | 42.44 | 1.91 |
| HPMCP 55 | 21.09 | 0.95 |

General

All the solutions were prepared using degassed deionized water under nitrogen. Vitamin A palmitate was shielded from light.

Preparation of a 12% solution of METHOCEL E15LV

Water (8 l) was heated to 85° C. METHOCEL E15LV powder (2.03 kg) was slowly added into the water while mixing with rapid agitation until a uniform suspension was obtained and thoroughly dispersed. Additional cold water (6.89 l) was quickly added to the suspension and the temperature was cooled to 25° C.

Preparation of a 15% solution of HPMCP

HPMCP powder (0.95 kg) was added to 4.28 l of 0.5 N NaOH with proper agitation and heated to 70° C. Hot (70° C.) water (1.1 l) was added after the powder completely dissolved. The solution was kept at 70° C. until used.

Preparation of the emulsion/suspension

BHA (0.045 kg) and 0.135 kg BHT were added to 1.46 kg vitamin A palmitate and mixed until a clear solution was formed. The solution was added to the METHOCEL E solution and emulsified for 30 minutes using a colloidal mill. The oil droplet size measured using a particle size analyzer (MALVERN Autosizer 2C manufactured by Malverne Instruments, Inc.) was 888 nm. Then, the emulsion was heated to 75° C. while slowly stirring (200 r.p.m.) with an anchor stir bar to form a suspension. The 70° C. HPMCP solution was added to the suspension and continuously stirred with an anchor agitator. The pH was adjusted to 6.9 with 0.5 l of 1 N NaOH (pH before: 5.28). The resulting suspension had a viscosity of 500 cps/70° C.

Spray drying

See below.

Formulation III

Composition

| Material | content (%) | weight (kg) |
| --- | --- | --- |
| Vitamin A palmitate 1.7 MIU/g | 32.47 | 1.46 |
| BHA | 1 | 0.045 |
| BHT | 3 | 0.135 |
| METHOCEL E15LV premium | 50.82 | 2.29 |
| Gum acacia | 12.7 | 0.58 |

General

All solutions were prepared using degassed deionized water under nitrogen. Vitamin A palmitate was shielded from light.

Preparation of a 10% solution of METHOCEL E

Water (6.2 l) was heated to 85° C. METHOCEL E15LV powder (2.29 kg) was slowly added into the water while mixing with rapid agitation until a uniform suspension was obtained. Additional cold water (14.41 l) was quickly added to the suspension and the temperature was cooled to 25° C.

Preparation of a 20% solution of gum acacia

Gum acacia powder (0.58 kg) was dissolved to 2.32 l cold water and heated to 70° C. The solution was kept at 70° C. until used.

Preparation of the emulsion/suspension

BHA (0.045 kg) and 0.135 BHT were added to 1.46 kg vitamin A palmitate and mixed until a clear solution was formed. The solution was added to the METHOCEL E solution and emulsified for 30 minutes with the colloidal mill. The oil droplet size measured using MALVERN Autosizer 2C was 854 nm. The emulsion was then heated to 75° C. while mixing with an anchor bar to form a suspension. The 70° C. gum acacia solution was added to the suspension and stirred with an anchor agitator. The pH was adjusted to 7.2 with 40 ml of 0.5 N NaOH (pH before: 6.37). The resulting suspension had a measured viscosity of 1060 cps/70° C.

Spray drying

See below.

Spray Drying Conditions for Formulations I, II and III

| Formulation Number | Feed Temp. (° C.) | Viscosity (cps) | pH | Inlet Air Temp. (° C.) | Outlet Air Temp. (° C.) | Inlet Air Flow m³/h | Wheel Speed (rpm) |
| --- | --- | --- | --- | --- | --- | --- | --- |
| I | 65 | 2,500/65° C. | — | 165 | 100 | 1,500 | 8,500 |
| II | 70 | 500/70° C. | 6.9 | 165 | 100 | 1,500 | 8,500 |
| III | 70 | 1,060/70° C. | 7.2 | 160 | 100 | 1,500 | 8,500 |

2% silicic acid (type FK 320 DS) was added in each trial. Pressure inside the tower was always about −4 mbar.

The subject invention has been described in terms of its preferred embodiments. However, one skilled in the art will recognize various alternative embodiments having read the specification. These variations are to be considered within the scope and spirit of the invention which is only to be limited by the claims which follow and their equivalents.

What is claimed is:

1. A powder composed of particles, the particles comprising an oleophilic substance encapsulated in a water soluble cellulose polymer, wherein the oleophilic substance is from about sixty-five percent to about eighty-five percent by weight of the powder, produced by:
  a) incorporating an oleophilic substance into an aqueous solution having a cellulose primary polymer dissolved therein, to form an aqueous mixture of the oleophilic substance in the solution, wherein the oleophilic substance in the mixture excluding overage is from about sixty-five percent to about eighty-five percent of the combined weight of the oleophilic substance and the polymer in the mixture;
  b) heat setting the primary polymer under mixing conditions while the primary polymer is in the aqueous mixture, to encapsulate the oleophilic substance within the primary polymer and form a primary particle in the aqueous mixture; and
  c) drying the aqueous mixture produced in step b) to yield the powder.

2. The powder of claim 1, wherein the cellulose primary polymer is selected from the group consisting of methylcellulose and hydroxypropyl methylcellulose.

3. The powder of claim 1, wherein the oleophilic substance is a fat-soluble vitamin.

4. The powder of claim 3, wherein the fat-soluble vitamin is selected from the group consisting of vitamins A, D, E and K.

5. The powder of claim 4, wherein the fat-soluble vitamin is vitamin E.

6. The powder of claim 2, wherein the cellulose primary polymer is hydroxypropyl methylcellulose.

7. A powder composed of particles, the particles comprising an oleophilic substance encapsulated in a water soluble cellulose polymer, wherein the oleophilic substance is from about sixty-five percent to about eighty-five percent by weight of the powder, produced by:
  a) incorporating an oleophilic substance into an aqueous solution having a cellulose primary polymer dissolved therein, to form an aqueous mixture of the oleophilic substance in the solution;
  b) heat setting the primary polymer under mixing conditions while the primary polymer is in the aqueous mixture, to encapsulate the oleophilic substance within the primary polymer and form a primary particle in the aqueous mixture;
  c) adding a secondary polymer to the aqueous mixture under mixing conditions to further encapsulate at least one primary particle within the secondary polymer, wherein the oleophilic substance in the mixture excluding overage is from about sixty-five percent to about eighty-five percent of the combined weight of the oleophilic substance, the primary polymer and the secondary polymer in the mixture; and
  d) drying the aqueous mixture produced in step c) to yield the powder.

8. The powder of claim 7, wherein the secondary polymer is selected from the group consisting of cellulose, cellulose derivatives, alginate, acacia, gelatin, maltodextrin, calcium lactate, and modified starches.

9. The composition of claim 8, wherein the cellulose derivative is selected from the group consisting of methylcellulose and hydroxypropyl methylcellulose.

10. The powder of claim 8, wherein the cellulose derivative is hydropropylmethyl cellulose phthalate.

11. The powder of claim 8, wherein the secondary polymer is a gelatin which is a fish gelatin.

12. The powder of claim 8, wherein the secondary polymer is maltodextrin.

13. The powder of claim 12, wherein the maltodextrin has a dextrose equivalent value of about 18.

14. The powder of claim 8, wherein the secondary polymer is a modified starch selected from the group consisting of pregelatinized corn starch and hydroxypropyl starch.

15. The powder of claim 7, wherein the secondary polymer encapsulates at least two primary particles.

16. The powder of claim 7, wherein the cellulose primary polymer is selected from the group consisting of methylcellulose and hydroxypropyl methylcellulose.

17. The powder of claim 16, wherein the primary polymer is hydroxypropyl methylcellulose.

18. The powder of claim 7, wherein the oleophilic substance is a fat-soluble vitamin.

19. The powder of claim 18, wherein the fat-soluble vitamin is selected from the group consisting of vitamins A, D, E and K.

20. The powder of claim 19, wherein the fat-soluble vitamin is vitamin E.

21. The powder of claim 1, wherein the oleophilic substance is from about seventy percent to about eighty-five percent by weight of the powder; and the oleophilic substance in the mixture excluding overage is from about seventy percent to about eighty-five percent of the combined weight of the oleophilic substance and the polymer in the mixture.

22. The powder of claim 21, wherein the oleophilic substance is from about seventy-five percent to about eighty-five percent by weight of the powder; and the oleophilic substance in the mixture excluding overage is from about seventy-five percent to about eighty-five percent of the combined weight of the oleophilic substance and the polymer in the mixture.

23. The powder of claim 22, wherein the oleophilic substance is from about eighty percent to about eighty-five percent by weight of the powder; and the oleophilic substance in the mixture excluding overage is from about eighty percent to about eighty-five percent of the combined weight of the oleophilic substance and the polymer in the mixture.

24. The powder of claim 7, wherein the oleophilic substance is from about seventy percent to about eighty-five percent by weight of the powder; and the oleophilic substance in the mixture excluding overage is from about seventy percent to about eighty-five percent of the combined weight of the oleophilic substance, the primary polymer and the secondary polymer in the mixture.

25. The powder of claim 24, wherein the oleophilic substance is from about seventy-five percent to about eighty-five percent by weight of the powder; and the oleophilic substance in the mixture excluding overage is from about seventy-five percent to about eighty-five percent of the combined weight of the oleophilic substance, the primary polymer and the secondary polymer in the mixture.

26. The powder of claim 25, wherein the oleophilic substance is from about eighty percent to about eighty-five percent by weight of the powder; and the oleophilic substance in the mixture excluding overage is from about eighty percent to about eighty-five percent of the combined weight of the oleophilic substance, the primary polymer and the secondary polymer in the mixture.

27. A powder composed of particles, the particles comprising an oleophilic substance encapsulated in a water soluble cellulose polymer, said powder produced by:
  a) incorporating an oleophilic substance into an aqueous solution having a primary polymer which is hydroxypropyl methylcellulose dissolved therein, to form an aqueous mixture of the oleophilic substance in the solution;

b) heat setting the primary polymer under mixing conditions while the primary polymer is in the aqueous mixture, to encapsulate the oleophilic substance within the primary polymer and form a primary particle in the aqueous mixture;

c) adding a secondary polymer to the aqueous mixture under mixing conditions to further encapsulate at least one primary particle within the secondary polymer; and d) drying the aqueous mixture produced in step c) to yield the powder.

28. A powder composed of particles, the particles comprising an oleophilic substance encapsulated in a water soluble cellulose polymer, said powder produced by:

a) incorporating an oleophilic substance into an aqueous solution having a primary polymer which is hydroxypropyl methylcellulose dissolved therein, to form an aqueous mixture of the oleophilic substance in the solution;

b) heat setting the primary polymer under mixing conditions while the primary polymer is in the aqueous mixture, to encapsulate the oleophilic substance within the primary polymer and form a primary particle in the aqueous mixture; and c) drying the aqueous mixture produced in step b) to yield the powder.

29. A powder composed of particles, the particles comprising an oleophilic substance encapsulated in a water soluble cellulose polymer, said powder produced by:

a) incorporating an oleophilic substance into an aqueous solution having a cellulose primary polymer dissolved therein, to form an aqueous mixture of the oleophilic substance in the solution;

b) heat setting the primary polymer under mixing conditions while the primary polymer is in the aqueous mixture, to encapsulate the oleophilic substance within the primary polymer and form a primary particle in the aqueous mixture;

c) adding a secondary polymer to the aqueous mixture under mixing conditions to further encapsulate at least one primary particle within the secondary polymer, wherein said secondary polymer is taken from the group consisting of hydropropyl methylcellulose phthalate, fish gelatin, maltodextrin, pregelatenized corn starch and hydroxypropyl starch; and d) drying the aqueous mixture produced in step c) to yield the powder.

* * * * *